United States Patent
Wu et al.

(10) Patent No.: US 9,897,585 B2
(45) Date of Patent: Feb. 20, 2018

(54) GEOMECHANICAL FLUID-SOLID COUPLING TESTING DEVICE FOR WATER INRUSH FROM COAL MINE COLLAPSE COLUMN

(71) Applicant: CHINA UNIVERSITY OF MINING AND TECHNOLOGY, BEIJING, Beijing (CN)

(72) Inventors: Qiang Wu, Beijing (CN); Lei Niu, Beijing (CN); Shucai Li, Beijing (CN); Shouqiang Liu, Beijing (CN); Yifan Zeng, Beijing (CN)

(73) Assignee: CHINA UNIVERSITY OF MINING AND TECHNOLOGY, BEIJING, Beijing (CN)

( * ) Notice: Subject to any disclaimer, the term of this patent is extended or adjusted under 35 U.S.C. 154(b) by 155 days.

(21) Appl. No.: 14/801,917

(22) Filed: Jul. 17, 2015

(65) Prior Publication Data
US 2016/0018379 A1 Jan. 21, 2016

(30) Foreign Application Priority Data
Jul. 18, 2014 (CN) .......................... 2014 1 0345227

(51) Int. Cl.
*G01N 17/00* (2006.01)
*G01N 33/24* (2006.01)

(52) U.S. Cl.
CPC .................................. *G01N 33/24* (2013.01)

(58) Field of Classification Search
CPC ....................................................... G01N 33/24
USPC ........................................... 73/118.01, 865.6
See application file for complete search history.

(56) References Cited

FOREIGN PATENT DOCUMENTS

| CN | 101308126 | * | 11/2008 | ............. G01N 33/00 |
| CN | 101576458 | * | 11/2009 | ............. G01N 3/12 |
| CN | 202204661 | * | 4/2012 | ............ G01M 10/00 |
| CN | 202339416 | * | 7/2012 | ............. G01V 9/00 |
| RU | 2394962 | * | 7/2010 | ............. E02D 19/00 |

* cited by examiner

*Primary Examiner* — Benjamin Schmitt
(74) *Attorney, Agent, or Firm* — Vidas Arrett & Steinkraus

(57) ABSTRACT

A geomechanical fluid-solid coupling testing device for water inrush from coal mine collapse column, which has a testing bed and a collapse column simulating device, wherein the testing bed has a box type structure with an opening at its top and is provided therein with multiple layers of similar materials in which a tunnel or a mining face can be dug out; and the collapse column simulating device comprises a plexiglass barrel with openings at both its top and bottom, the plexiglass barrel is provided at its top opening with a plexiglass lifting device and a hard plastic baffle, and the plexiglass lifting device is provided with a lifting level which is connected with a lifting rope.

17 Claims, 4 Drawing Sheets

GEOMECHANICAL FLUID-SOLID COUPLING TESTING DEVICE FOR WATER INRUSH FROM COAL MINE COLLAPSE COLUMN

CROSS-REFERENCE TO RELATED APPLICATIONS

This application claims the benefit of Chinese Patent Application No. CN201410345227.X, filed Jul. 18, 2014, the entire content of which is hereby incorporated herein by reference.

FIELD OF THE INVENTION

The present invention relates to a geomechanical testing technology, and specifically to a geomechanical fluid-solid coupling testing device for water inrush from coal mine collapse column.

BACKGROUND OF THE INVENTION

The karstic collapse column is a common geological structure in North China type coal mines. Most collapse column is not water conductive, but a small few collapse column with high water conductivity caused serious water inrush disasters. The collapse column water inrush has characteristics of high water amount, high speed, high amount of protrusions, etc, resulting in serious threat to mine safety.

Nowadays, the problems related to the collapse column have attracted attention from the engineering and science & technology personnel. The researchers in out country have studied a lot on the model testing work. However, there are obvious defects.

The prior research is focused on the forming mechanism, prediction and management of the collapse column. However, the research on the water inrush mechanism of the collapse column, especially the lag water inrush mechanism thereof, is insufficient, and there is no substantial research on 3D similarity physics simulating test. Particularly, most research is not related to the apparatus and processing for forming the collapse column.

SUMMARY OF THE INVENTION

An objective of the present invention is to provide a geomechanical fluid-solid coupling testing device for water inrush from coal mine collapse column, which can simulate the karstic collapse column construction process mechanics and deformation rules with the influences of tunnel digging or mining on a mining face or other factors.

The objective of the present invention is achieved by the following technical solution:

According to the present invention, a geomechanical fluid-solid coupling testing device for water inrush from coal mine collapse column comprises a testing bed and a collapse column simulating device, wherein the testing bed has a box type structure with an opening at its top and is provided therein with multiple layers of similar materials in which a tunnel or a mining face can be dug out;

The collapse column simulating device comprises a plexiglass barrel with openings at both its top and bottom, the plexiglass barrel is provided at its top opening with a plexiglass lifting device and a hard plastic baffle, and the plexiglass lifting device is provided with a lifting level which is connected with a lifting rope. Plexiglass a solid transparent plastic made of polvmethyl methacrylate and sold under the trademark PLEXIGLAS®.

As can be seen from the above technical solution provided in the present invention, the geomechanical fluid-solid coupling testing device for water inrush from coal mine collapse column provided in the embodiment of the present invention comprises a testing bed and a collapse column simulating device, and the testing bed has a box type structure with an opening at its top, the collapse column simulating device comprises a plexiglass barrel with openings at both its top and bottom, the plexiglass barrel is provided at its top opening with a plexiglass lifting device and a hard plastic baffle, and the plexiglass lifting device is provided with a lifting level which is connected with a lifting rope. It has a simple structure and enables realistic simulation, and can be used for simulating a construction process in a situation of tunnel digging or coal seam mining, for example, for collecting water inrush omen information, and for studying on surrounding rock mechanics, deformation and collapse column seepage rules during construction, thus facilitating safe construction and early warning in practical engineering.

Figure 1:
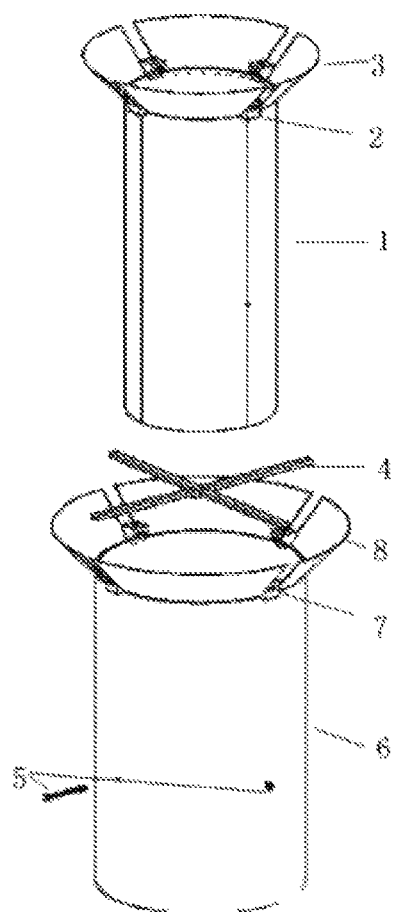
FIG. 1 is a diagram of portions of a collapse column simulating device according to an embodiment of the present invention.
Figure 2:
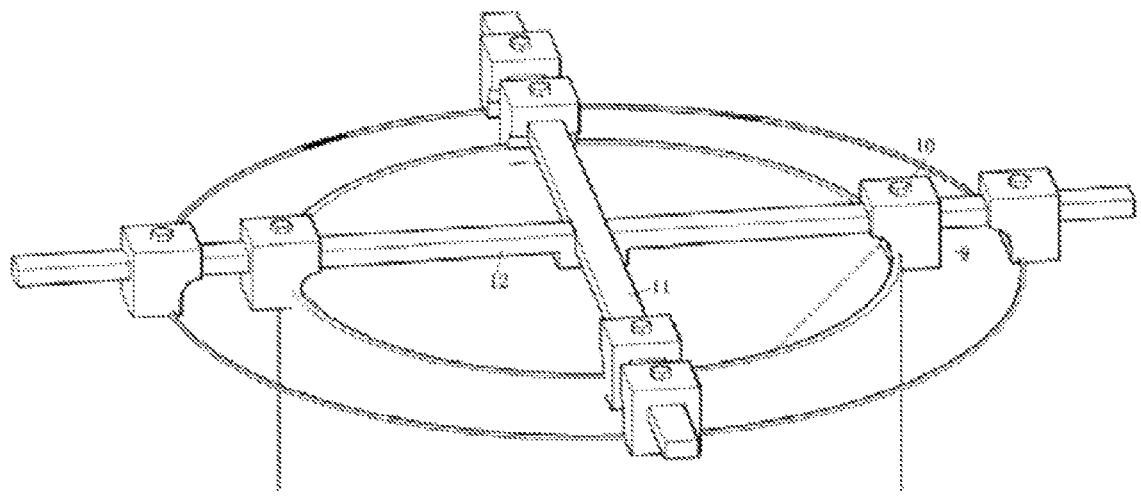
FIG. 2 is a diagram of a lifting device according to an embodiment of the present invention.
Figure 3:
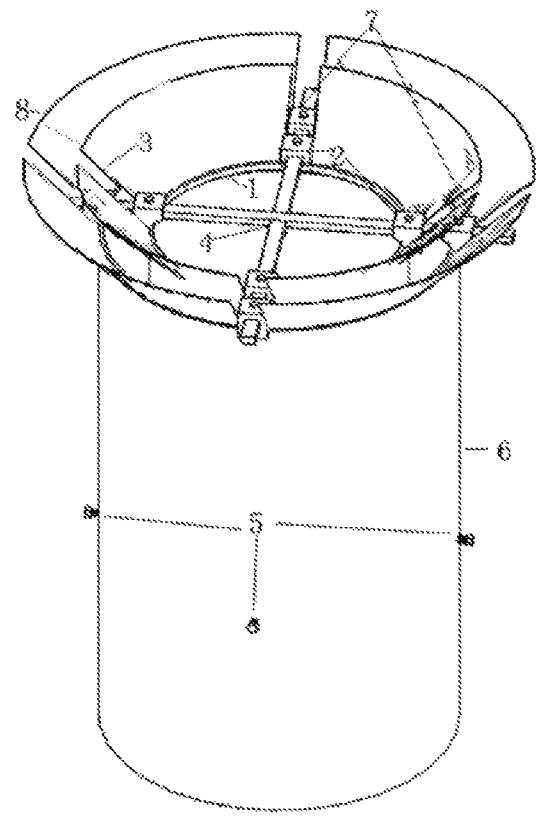
FIG. 3 is a diagram of a full-section water conductive collapse column simulating device after assembling according to an embodiment of the present invention.
Figure 4:
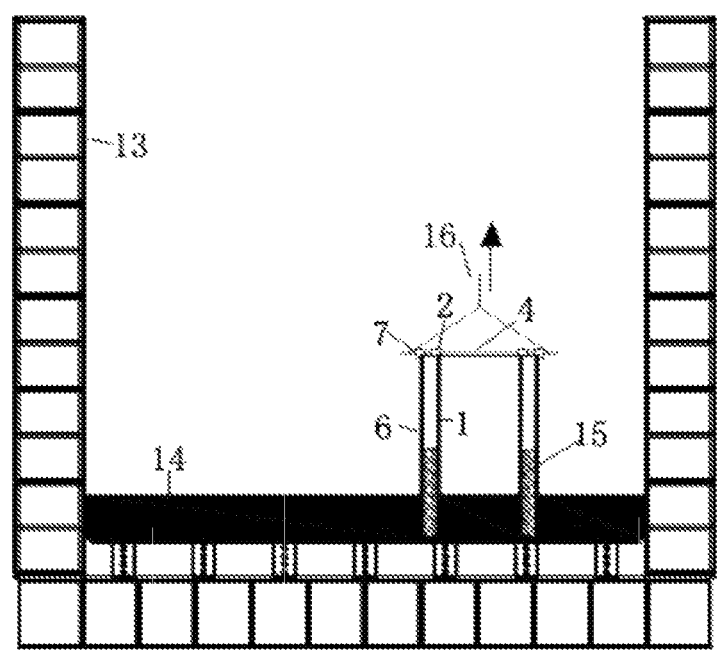
FIG. 4 is a flowchart diagram of a method for forming an edge water conductive collapse column according to an embodiment of the present invention.
Figure 5:
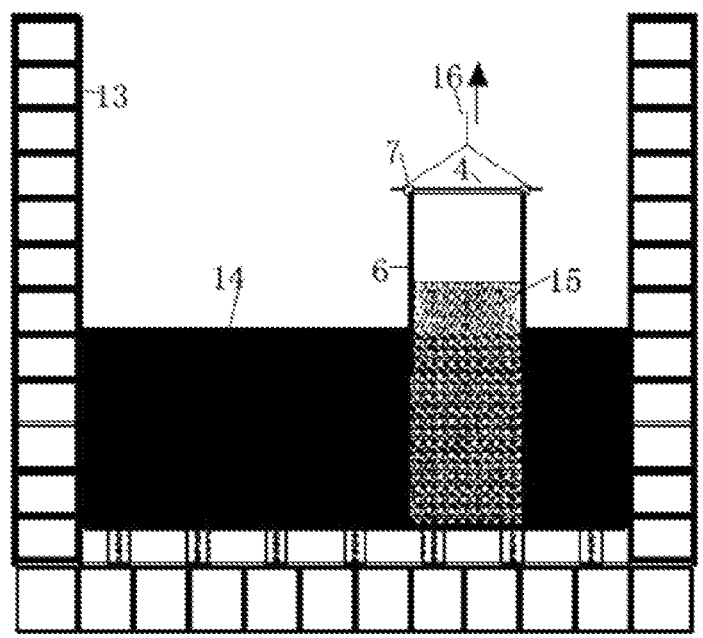
FIG. 5 is a diagram of a first cycle in formation of an edge water conductive collapse column according to an embodiment of the present invention.
Figure 6:
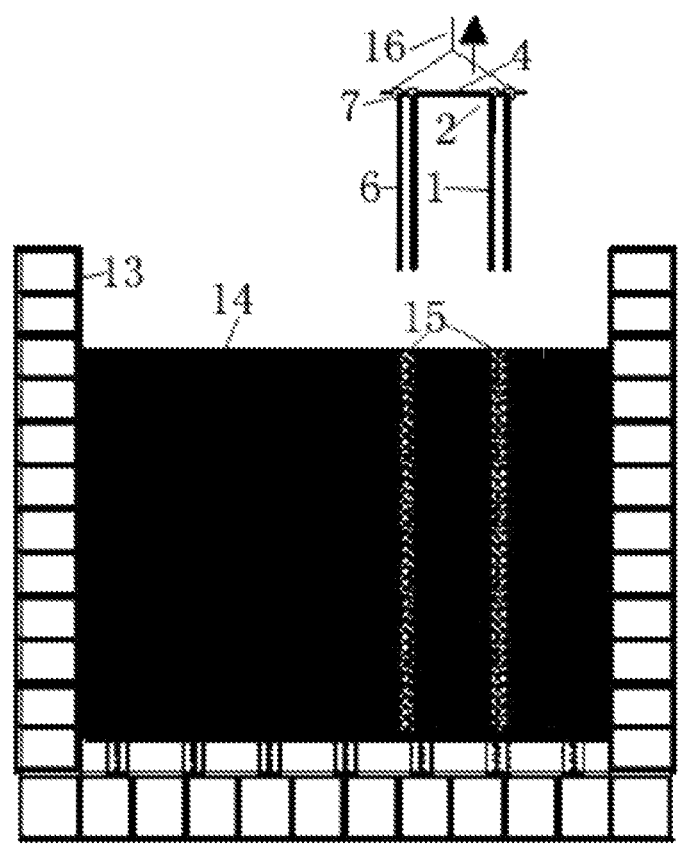
FIG. 6 is a diagram of a middle cycle in formation of a full-section water conductive collapse column according to an embodiment of the present invention.

Reference numerals in the figures are shown as following: an inner layer plexiglass barrel 1, an inner layer plexiglass lifting device 2, an inner layer hard plastic baffle 3, a lifting level 4, a connecting screw rod 5, an outer layer plexiglass barrel 6, an outer layer plexiglass lifting device 7, an outer layer hard plastic baffle 8, a plexiglass lifting component 9, a gland nut 10, a straight lifting level 11, a bended lifting level 12, a testing bed 13, a similar material 14, a loose granular material 15, and a lifting rope 16.

DESCRIPTION OF THE PREFERRED EMBODIMENTS

Hereinafter, the embodiments of the present invention will be further described in detail.

A preferred embodiment of the geomechanical fluid-solid coupling testing device for water inrush from coal mine collapse column according to the present invention comprising:

a testing bed and a collapse column simulating device, wherein the testing bed has a box type structure with an opening at its top and is provided therein with multiple layers of similar materials in which a tunnel or a mining face can be dug out;

wherein the collapse column simulating device comprises a plexiglass barrel with openings at both its top and bottom, the plexiglass barrel is provided at its top opening with a plexiglass lifting device and a hard plastic baffle, and the plexiglass lifting device is provided with a lifting level which is connected with a lifting rope.

The lifting level comprises a straight lifting level and a bended lifting level which are arranged perpendicularly, the plexiglass lifting device comprises 4 plexiglass lifting components fixed at the top opening of the plexiglass barrel, and the straight lifting level and the bended lifting level pass through the plexiglass lifting components and then are fixed with gland nuts.

The plexiglass barrel has a structure of single layer or multiple layers, and the multiple layers of plexiglass barrel are connected therebetween by a connecting screw rod.

In a full-section water-conductive collapse column testing of the device, the collapse column simulating device is selected to have a structure of single layer of plexiglass barrel and is placed at the bottom of the testing bed, with the similar material for a non-water-conductive segment filling the outer portion of the plexiglass barrel and a loose granular material for the water conductive segment filling the inner portion of the plexiglass barrel, and the full-section water-conductive collapse column is formed in the similar material after the plexiglass barrel is removed.

In an edge water-conductive collapse column testing of the device, the collapse column simulating device is selected to have a structure of double layers of plexiglass barrel and is placed at the bottom of the testing bed, with the similar material for a non-water-conductive segment filling the outer portion of the outer layer plexiglass barrel and the inner portion of the inner layer plexiglass barrel and a loose granular material for the water conductive segment filling the portion between the two layer plexiglass barrels, and the edge water-conductive collapse column is formed in the similar material after the plexiglass barrel is removed.

During formation of the water conductive collapse column, a method of layer-by-layer filling and tamping and layer-by-layer lifting of the collapse column simulating device is used.

The geomechanical fluid-solid coupling testing device for water inrush from coal mine collapse column according to the present invention has a simple structure and enables realistic simulation, and can be used for simulating a construction process in a situation of tunnel digging or coal seam mining, for example, for collecting water inrush omen information, and for studying on surrounding rock mechanics, deformation and collapse column seepage rules during construction, thus facilitating formation of karstic collapse column in a similar simulating test for safe construction and early warning in practical engineering.

The principle of the present invention are explained as following:

assembling the collapse column simulating device based on the test design according to the engineering background, wherein a plexiglass barrel is used for simulating the full-section water conductive collapse column, having an outer diameter equal to the collapse column diameter as test-designed; two plexiglass barrels are used for simulating the edge water conductive collapse column, having an outer diameter of the outer layer barrel equal to the collapse column diameter and an inner diameter of the inner layer barrel equal to the diameter at the middle water inconductive segment, and the two barrels are connected with each other by a screw rod via a threaded hole away from the barrel bottom by 30 cm; four plexiglass lifting devices are evenly distributed and, by means of the glass cement, are adhered to the top of the plexiglass barrel with an adhering height of 1 cm;

paving the similar material, wherein the similar material is paved in the testing bed layer by layer according to the rock-soil mass strength and hydro-physics characteristics in the engineering background, and can be paved according to the actual rock-soil layer dip angle;

after the respective similar simulating material as paved in the testing box reaches the position of the bottom of the collapse column as test-designed, placing the collapse column simulating device according to the angle and azimuth in the engineering background;

filling the position of the water conductive segment as designed in the inside of the apparatus (i.e. the full section in the full-section water conductive collapse column testing, or the position between the two barrels in the edge water conductive collapse column testing) with a loose granular material for testing by 40 cm, and paving the non-water-conductive segment as designed (i.e. the outer layer of the plexiglass barrel in the full-section water conductive collapse column testing, and additionally comprising the inner portion of the inner layer barrel in the edge water conductive collapse column testing) with the similar simulating material by 20 cm, thus fixing the testing device; and inserting a metal lifting level centrally into the plexiglass lifting device, fastening the screw to fix the lifting level, binding two lifting ropes with a common end on two ends of the lifting level, raising the lifting rope by manual or mechanical power, lifting the device by 10 cm with a collapse column angle as test-designed, rotating the lifting level such that the loose granular material is evenly distributed and the contact face between the outside of the collapse column and the similar material is loose and rough, and removing the lifting rope and the lifting level; filling the respective positions inside and outside the collapse column with the loose granular material and the similar simulating material by 10 cm, and rotating the hard plastic baffle during filling such that the space at the respective position is maximized (during filling of the loose granular material, the outer layer baffle faces outward and the inner layer baffle faces inward; while during filling of the similar material, the outer layer baffle faces inward and the inner layer baffle faces outward); then performing the raising and the filling circularly until the bottom face of the device is at a position by 20 cm with respect to the upper edge of the collapse column as test-designed, filling the outer layer similar simulating material (additionally plus the inner layer similar simulating material for the edge water conductive collapse column) to a position of the upper edge of the collapse column as designed, and removing the device.

The similar material, the loose granular material and the testing bed in the present invention belong to prior materials and apparatuses, and will not be further described in detail.

In the present invention, according to the shape and size of the collapse column in the practical engineering, by a similarity ratio conversion, the loose granular material with a good water conductivity is used to simulate the water conductive segment in the collapse column and the similar simulating material with a relatively poor water conductivity is used to simulate the water inconductive segment in the collapse column; the collapse column simulating device is used to position and fix the respective materials; according to the requirements of the test design, the process of forming the collapse column is divided into several cycles to satisfy the prior construction condition and enable the testing purposes, the operations of inside filling, outside filling, device lifting, etc. are performed in the cycles, respectively, and the collapse column is formed by repeating the cycles; after the respective materials are dried and bonded, the water conduction is performed to the aquifer according to the test design, thus completing the respective water inrush test.

In the present invention, the device and method for forming the karstic collapse column in the model test are studied, and the problems of formation and simulation of karstic collapse column in the karstic collapse column water inrush test are solved. The karstic collapse column simulated at the respective position according to the engineering background and test design requirements, compared with the prior study, fills in a gap in the karstic collapse column water inrush mechanism 3D geomechanical testing, is more realistic to that in the practical engineering, and is more adaptable in application to geomechanical similarity simulation testing.

In the present invention, the problems of formation and simulation of karstic collapse column in the karstic collapse column water inrush test are solved, and the following advantages are presented as following:

enabling successful simulation to karstic collapse column in different dip angle and different size;

enabling simulation to both the full-section water conductive collapse column and the edge water conductive collapse column;

enabling successful simulation to the contact face between the collapse column and surrounding rock mass;

ensuring successful paving of the similar simulating material in which the materials inside and outside the device can remain stable in accordance with the test design;

facilitating construction order arrangement and having a relatively simple construction processing; and enabling the formed karstic collapse column to simulate the karstic collapse column construction process mechanics and deformation rules, etc. with the influences of tunnel digging or mining on a mining face or other factors.

EXAMPLE

As shown in FIGS. 1 to 7, the device of the present invention comprises a fluid-solid coupling model testing bed 13 and a collapse column simulating system. The testing bed is a rigid transparent bed. The collapse column simulating system comprises a collapse column simulating device and a collapse column simulating material. The collapse column simulating material comprises a loose granular material 15 for simulating the collapse column water conductive segment and a similar material 14 for simulating the collapse column non-water-conductive segment. The collapse column simulating device comprises a plexiglass barrel 6, a plexiglass lifting device 7 and a hard plastic baffle 8. When simulating the edge water conductive collapse column, it further needs a connecting screw rod 5 to connect the inner and outer plexiglass barrels 1 and 6. The plexiglass lifting device 7 comprises a plexiglass lifting component 9 and a gland nut 10. A lifting level 4 comprising a straight lifting level 11 and a bended lifting level 12 can be used to fasten a lifting rope 16. Also, if the lifting rope 16 is lifted, the whole device can be lifted.

Figure 7:
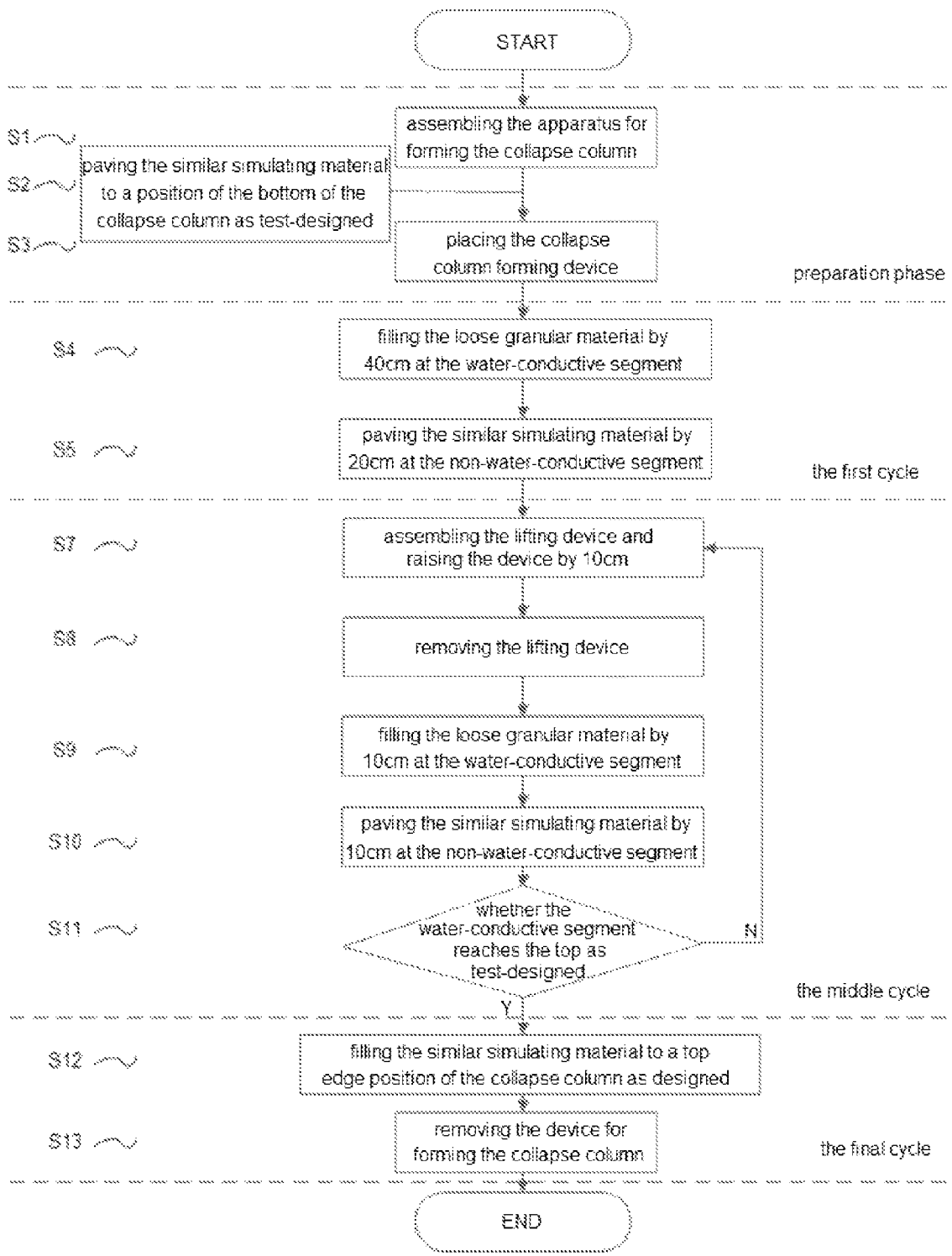
FIG. 7 is a diagram of a final cycle in formation of an edge water conductive collapse column according to an embodiment of the present invention.

The collapse column simulating method comprises the following steps:

A. according to the testing requirements, selecting the plexiglass barrels 1 and 6 having respective sizes and assembling the connecting screw rod 5, the plexiglass lifting devices 2 and 7, corresponding to S1 in FIG. 7;

B. in the testing box, paving the respective similar simulating material 14 to a position and an angle of the bottom of the collapse column as test-designed, corresponding to S2 in FIG. 7;

C. hoisting the installed collapse column simulating device to a test design position (S3);

D. paving the loose granular material 15 by 40 cm at the water conductive segment, tamping it to fix the collapse column simulating device, corresponding to S4 in FIG. 7;

E. paving the similar material 14 at the non-water-conductive segment based on the test design, and during paving, rotating the respective hard plastic baffles 3 and 8 such that the space at the respective position is maximized, thus stabilizing the collapse column simulating device, corresponding to S5 in FIG. 7;

F. waiting for 2 hours, and after the similar material is substantially cemented, installing the metal lifting level 4, rotating and raising the simulating device by 10 cm such that the loose granular material and the similar simulating material are loosely and roughly contacted at the boundary, and removing the metal lifting level 4, corresponding to S7 and S8 in FIG. 7;

G. filling the simulating materials 14 and 15, respectively, by 10 cm, assembling the lifting level and lifting, corresponding to S9 and S10 in FIG. 7; and H. repeating the filling and lifting until the top face of the collapse column as test-designed is reached, removing the collapse column simulating device out of the testing bed 13, and after the similar material is cemented and dried, completing formation of the collapse column.

The above description is just for preferred specific embodiment(s) of the present invention. However, the protection scope of the present invention is not limited thereto. Any variation or substitution within the technical scope as disclosed by the present invention easily conceivable by those skilled in the art should fall into the protection scope of the present invention. Therefore, the protection scope of the present invention should be defined by the protection scope of the claims.

To be claimed:

1. A geomechanical fluid-solid coupling testing device for water inrush from coal mine collapse column, comprising a testing bed and a collapse column simulating device, wherein the testing bed has a box type structure with an opening at its top and is provided therein with multiple layers of karstic simulating similar materials in which a tunnel or a mining face can be dug out; and wherein the collapse column simulating device comprises a plexiglass barrel with openings at a top and a bottom of the plexiglass barrel, the plexiglass barrel is provided at its top opening with a plexiglass lifting device and a hard plastic baffle, and the plexiglass lifting device is provided with a lifting level which is connected with a lifting rope.

2. The geomechanical fluid-solid coupling testing device for water inrush from coal mine collapse column according to claim 1, wherein the lifting level comprises a straight lifting level and a bended lifting level which are arranged perpendicularly, the plexiglass lifting device comprises four plexiglass lifting components fixed at the top opening of the plexiglass barrel, and the straight lifting level and the bended lifting level pass through the plexiglass lifting components and are fixed with gland nuts.

3. The geomechanical fluid-solid coupling testing device for water inrush from coal mine collapse column according to claim 2, wherein the plexiglass barrel has a structure of single layer or multiple layers, and the multiple layers of plexiglass barrel are connected therebetween by a connecting screw rod.

4. The geomechanical fluid-solid coupling testing device for water inrush from coal mine collapse column according to claim 3, wherein in a full-section water-conductive collapse column testing of the device, the collapse column simulating device is selected to have a structure of single layer of plexiglass barrel and is placed at the bottom of the testing bed, with the karstic simulating similar material for a non-water-conductive segment filling the outer portion of the plexiglass barrel and a loose granular material for the water conductive segment filling the inner portion of the plexiglass barrel, and the full-section water-conductive collapse column is formed in the karstic simulating similar material after the plexiglass barrel is removed.

5. The geomechanical fluid-solid coupling testing device for water inrush from coal mine collapse column according to claim 4, wherein during formation of the water conductive collapse column, a layer-by-layer filling and tamping and layer-by-layer lifting of the collapse column simulating device is used.

6. The geomechanical fluid-solid coupling testing device for water inrush from coal mine collapse column according to claim 3, wherein in an edge water-conductive collapse column testing of the device, the collapse column simulating device is selected to have a structure of double layers of plexiglass barrel and is placed at the bottom of the testing bed, with the karstic simulating similar material for a non-water-conductive segment filling the outer portion of the outer layer plexiglass barrel and the inner portion of the inner layer plexiglass barrel and a loose granular material for the water conductive segment filling the portion between the two layer plexiglass barrels, and the edge water-conductive collapse column is formed in the karstic simulating similar material after the plexiglass barrel is removed.

7. The geomechanical fluid-solid coupling testing device for water inrush from coal mine collapse column according to claim 6, wherein during formation of the water conductive collapse column, a layer-by-layer filling and tamping and layer-by-layer lifting of the collapse column simulating device is used.

8. A testing device comprising:
a testing bed having a cavity and a first karstic simulating material in said cavity;
a collapse column simulating device comprising a tubular barrel, at least a portion of said tubular barrel oriented in said cavity, a second karstic simulating material in said tubular barrel; and
a lifting device arranged to lift said collapse column simulating device.

9. The testing device of claim 8, wherein said second karstic simulating material comprises a granular material.

10. The testing device of claim 8, wherein said second karstic simulating material is more water conductive than said first karstic simulating material.

11. The testing device of claim 8, wherein said tubular barrel is open at a top and a bottom.

12. The testing device of claim 8, wherein said tubular barrel comprises plexiglass.

13. The testing device of claim 8, said collapse column simulating device comprising a lifting level, said lifting device attached to said lifting level.

14. The testing device of claim 8, wherein said tubular barrel comprises an outer tubular barrel, said collapse column simulating device further comprising an inner tubular barrel.

15. The testing device of claim 14, wherein said second karstic simulating material is positioned between said outer tubular barrel and said inner tubular barrel.

16. The testing device of claim 14, said collapse column simulating device comprising a lifting level attached to said outer tubular barrel and to said inner tubular barrel, said lifting device attached to said lifting level.

17. The testing device of claim 8, wherein said collapse column simulating device contacts a base of said cavity.

\* \* \* \* \*